(12) United States Patent
Omara et al.

(10) Patent No.: US 8,846,820 B2
(45) Date of Patent: Sep. 30, 2014

(54) ACTIVATED SILANE COMPOUND, RUBBER COMPOSITION USING THE SAME AND TIRE

(71) Applicant: Bridgestone Corporation, Chuo-Ku (JP)

(72) Inventors: Tetsuya Omara, Tokyo (JP); Kouichi Morita, Tokyo (JP); Uchu Mukai, Tokyo (JP)

(73) Assignee: Bridgestone Corporation, Tokyo (JP)

( * ) Notice: Subject to any disclaimer, the term of this patent is extended or adjusted under 35 U.S.C. 154(b) by 0 days.

(21) Appl. No.: 13/896,718

(22) Filed: May 17, 2013

(65) Prior Publication Data

US 2013/0253113 A1 Sep. 26, 2013

Related U.S. Application Data

(63) Continuation of application No. 12/295,648, filed as application No. PCT/JP2007/057559 on Apr. 4, 2007, now Pat. No. 8,476,374.

(30) Foreign Application Priority Data

Apr. 5, 2006 (JP) ................. 2006-104506

(51) Int. Cl.
| | |
|---|---|
| C08C 19/00 | (2006.01) |
| C08F 8/00 | (2006.01) |
| C08F 8/42 | (2006.01) |
| C08K 5/56 | (2006.01) |
| C08K 5/548 | (2006.01) |
| B60C 1/00 | (2006.01) |
| C08K 5/544 | (2006.01) |
| C07F 7/18 | (2006.01) |
| C08K 5/54 | (2006.01) |
| C08K 5/5419 | (2006.01) |

(52) U.S. Cl.
CPC . *C08K 5/56* (2013.01); *C08K 5/548* (2013.01); *B60C 1/0025* (2013.04); *B60C 1/0016* (2013.04); *C08K 5/544* (2013.01); *C07F 7/1836* (2013.01); *C08K 5/54* (2013.01); *B60C 1/00* (2013.01); *C08K 5/5419* (2013.01); *C08K 5/5442* (2013.01)
USPC ........ 525/342; 525/242; 526/335; 526/348.6; 524/443; 524/261; 524/492

(58) Field of Classification Search
CPC .............. C08C 19/00; C08F 8/00; C08F 8/42
USPC ............... 525/342, 242, 335, 348.6; 524/443, 524/261, 492; 526/335, 348.6
See application file for complete search history.

(56) References Cited

U.S. PATENT DOCUMENTS

| | | | |
|---|---|---|---|
| 4,137,249 | A | 1/1979 | Wohlfarth et al. |
| 4,400,327 | A | 8/1983 | Baskent et al. |
| 4,489,199 | A | 12/1984 | Wengrovius |
| 6,069,186 | A | 5/2000 | Okinoshima et al. |
| 6,191,247 | B1 | 2/2001 | Ishikawa et al. |
| 6,380,411 | B1 | 4/2002 | Luginsland et al. |
| 2003/0015272 | A1 | 1/2003 | Teratani et al. |
| 2005/0020757 | A1 | 1/2005 | Ozawa et al. |
| 2005/0159554 | A1* | 7/2005 | Endou et al. ............. 525/242 |

FOREIGN PATENT DOCUMENTS

| | | |
|---|---|---|
| EP | 1 449 857 A1 | 8/2004 |
| EP | 1 505 087 A1 | 2/2005 |
| JP | 49-31765 A | 3/1974 |
| JP | 51-146426 A | 12/1976 |
| JP | 58-149912 A | 9/1983 |
| JP | 60-90258 A | 5/1985 |
| JP | 10-67887 A | 3/1998 |
| JP | 10-182885 | 7/1998 |
| JP | 11-181161 | 7/1999 |
| JP | 11-302348 A | 11/1999 |
| JP | 2000-086905 | 3/2000 |
| JP | 2005-247923 A | 9/2005 |
| RU | 2 257 390 C2 | 8/2002 |
| RU | 2267493 C2 | 1/2004 |
| WO | 03/046020 A1 | 6/2003 |
| WO | 03/087171 A1 | 10/2003 |

OTHER PUBLICATIONS

Official Action corresponding to Russian Patent Application No. 2008143305/04(056381).
Japanese Office Action issued on Nov. 6, 2012 in Japanese Application No. 2008-510920.

\* cited by examiner

*Primary Examiner* — James J Seidleck
*Assistant Examiner* — Deve E Valdez
(74) *Attorney, Agent, or Firm* — Sughrue Mion, PLLC

(57) ABSTRACT

The present invention relates to an activated silane compound obtained by reacting a hydrocarbyloxysilane compound with an organic metal compound in an organic solvent, and enhancing interaction of silica with carbon black and improving the fracture characteristic, the abrasion resistance and the low heating property provide an activated silane compound which can be reduced in a blending amount, a rubber composition prepared by blending it as a silane coupling agent and a pneumatic tire prepared by using the above rubber composition, which is excellent in a durability, a low heating property and the like.

7 Claims, No Drawings

ACTIVATED SILANE COMPOUND, RUBBER COMPOSITION USING THE SAME AND TIRE

CROSS REFERENCED TO RELATED APPLICATIONS

This is a continuation application of U.S. application Ser. No. 12/295,648, filed Oct. 1, 2008, which is a 371 of PCT/JP2007/057559 filed Apr. 4, 2007, which claims priority from JP 2006-104506 filed Apr. 5, 2006. The above-noted applications are incorporated herein by reference in their entirety.

BACKGROUND OF THE INVENTION

The present invention relates to an activated silane compound which is enhanced in a reactivity with silica, a rubber composition prepared by using the same and a tire prepared by using the above rubber composition for at least a part of members thereof.

RELATED ART

In general, various silane coupling agents are used in silica-blended rubber compositions for the purpose of enhancing vulcanization physical properties such as an elastic modulus, an tensile strength, an elongation at break, an abrasion resistance and the like. However, a reactivity of silane coupling agents to silica is not yet necessarily satisfactory, and various improvements have so far been investigated.

Proposed in a patent document 1 is a method in which in a rubber composition prepared by blending silica and a silane coupling agent, reaction of the silane coupling agent with silica is accelerated by adding the silane coupling agent and a silanol condensation catalyst in kneading rubber to reduce a blending amount of the silane coupling agent.

In the above method, however, since the silanol condensation catalyst is added in kneading rubber, a contact efficiency of the catalyst with the silane coupling agent is not necessarily satisfactory, and reaction of the silane coupling agent with silica can not sufficiently be accelerated.

Further, proposed is a production process in which in the middle of and/or after finishing primary modification in which a hydrocarbyloxysilane compound is reacted with the active end of a conjugated diene base polymer having an active end, condensation accelerating agent such as a hydrocarbyloxysilane compound and the like is further added to a reaction system to carry out secondary modification, whereby interaction of silica with carbon black is enhanced to obtain a modified polymer improved in a fracture characteristic, an abrasion resistance and a low heating property (refer to a patent document 2 or 3).

In the above method, however, the modified polymer rubber described above has to be used, and it can not be applied to usual conjugated diene base polymer rubber compositions.

Accordingly, a silane coupling agent which enhances interaction with silica and the like without using a specific modified polymer rubber and which can be reduced in a blending amount has so far been desired.

Patent document 1: Japanese Patent Application Laid-Open No. 67887/1998
Patent document 2: WO2003/046020 pamphlet
Patent document 3: WO2003/087171 pamphlet

DISCLOSURE OF THE INVENTION

The present invention has been made under the situation described above, and an object of the present invention is to provide an activated silane compound which can be reduced in a blending amount by enhancing interaction of silica with carbon black and improving the fracture characteristic, the abrasion resistance and the low heating property, a rubber composition prepared by blending the above compound as a silane coupling agent and a pneumatic tire prepared by using the above rubber composition, which is excellent in a durability, a low heating property and the like.

Intensive researches repeated by the present inventors in order to achieve the object described above have resulted in finding that the object can be achieved by using a reaction product of a specific silane compound with an organic metal compound. The present invention has been completed based the above knowledge.

That is, the present invention provides an activated silane compound obtained by reacting a hydrocarbyloxysilane compound with an organic metal compound in an organic solvent, a rubber composition containing 10 to 180 parts by mass of silica per 100 parts by mass of a rubber component and 1 to 20 mass % of the activated silane compound based on silica and a tire prepared by using the above rubber composition for at least a part of members thereof.

BEST MODE FOR CARRYING OUT THE INVENTION

The present invention relates to an activated silane compound obtained by reacting a hydrocarbyloxysilane compound with an organic metal compound in an organic solvent, and the above compound is blended as a silane coupling agent into a silica-blended rubber composition.

In this connection, the hydrocarbyloxysilane compound is preferably at least one compound selected from the group consisting of (1) a compound represented by Formula (I), (2) a compound represented by Formula (II), (3) a compound represented by Formula (III), (4) a compound represented by Formula (IV), (5) a compound represented by Formula (V) and partially condensed compounds thereof.

In this regard, the partially condensed compound shows a compound obtained by turning a part (not the whole part) of SiOR in the hydrocarbyloxysilane compound into an Si—O—Si bond by condensation.

(1) Compound Represented by Formula (I)

(wherein $A^1$ is a monovalent group having at least one functional group selected from (thio)epoxy group, (thio)isocyanate group, (thio)ketone group, (thio)aldehyde group, an imine residue, amide group, a trihydrocarbyl isocyanurate residue, a (thio)carboxylic ester residue, a metal salt of a (thio)carboxylic ester residue, a carboxylic anhydride residue, a carboxylic halide residue and a dihydrocarbyl carbonate residue; $R^1$ is a single bond or a divalent inactive hydrocarbon group; $R^2$ and $R^3$ each represent independently a monovalent aliphatic hydrocarbon group having 1 to 20 carbon atoms or a monovalent aromatic hydrocarbon group having 6 to 18 carbon atoms; n is an integer of 0 to 2; when $R^2$ is present in a plural number, plural $R^2$ may be the same or different, and when $OR^3$ is present in a plural number, plural $OR^3$ may be the same or different; and an active proton and an onium salt are not contained in a molecule).

(2) Compound Represented by Formula (II)

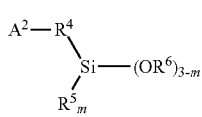
(II)

(wherein $A^2$ is a monovalent group having at least one functional group selected from a cyclic tertiary amine residue, a non-cyclic tertiary amine residue, a pyridine residue, sulfide group, multisulfide group and nitrile group; $R^4$ is a single bond or a divalent inactive hydrocarbon group; $R^5$ and $R^6$ each represent independently a monovalent aliphatic hydrocarbon group having 1 to 20 carbon atoms or a monovalent aromatic hydrocarbon group having 6 to 18 carbon atoms; m is an integer of 0 to 2; when $R^5$ is present in a plural number, plural $R^5$ may be the same or different, and when $OR^6$ is present in a plural number, plural $OR^6$ may be the same or different; and an active proton and an onium salt are not contained in a molecule).

(3) Compound Represented by Formula (III)

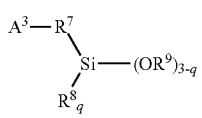
(III)

(wherein $A^3$ is a monovalent group having at least one functional group selected from alkoxy group, hydroxy group, thiol group, a primary amine residue and an onium salt thereof, a cyclic secondary amine residue and an onium salt thereof, a non-cyclic secondary amine residue and an onium salt thereof, an onium salt of a cyclic tertiary amine residue, an onium salt of a non-cyclic tertiary amine residue, a group having an aryl or arylalkyl Sn bond, sulfonyl group, sulfinyl group and nitrile group; $R^7$ is a single bond or a divalent inactive hydrocarbon group; $R^8$ and $R^9$ each represent independently a monovalent aliphatic hydrocarbon group having 1 to 20 carbon atoms or a monovalent aromatic hydrocarbon group having 6 to 18 carbon atoms; q is an integer of 0 to 2; when $R^8$ is present in a plural number, plural'$R^8$ may be the same or different, and when $OR^9$ is present in a plural number, plural $OR^9$ may be the same or different).

(4) Compound Represented by Formula (IV)

$(R^{10}O)_3Si—R^{11}—S_k—R^{11}—Si(OR^{10})_3$ (IV)

(wherein $R^{10}$ is a monovalent hydrocarbon group having 1 to 4 carbon atoms; $R^{11}$ is a divalent hydrocarbon group having 1 to 9 carbon atoms; k is a positive number of 1 or more and has distribution; $R^{10}O$ in $(R^{14}O)_3$ may be the same or different).

(5) Compound Represented by Formula (V)

$R^{12}_j—Si—(OR^{13})_{4-j}$ (V)

(wherein $R^{12}$ and $R^{13}$ each represent independently a monovalent aliphatic hydrocarbon group having 1 to 20 carbon atoms or a monovalent aromatic hydrocarbon group having 6 to 18 carbon atoms; j is an integer of 0 to 2; when plural $R^{12}$ are present, plural $R^{12}$ may be the same or different, and when plural $OR^{13}$ are present, plural $OR^{13}$ may be the same or different; and an active proton and an onium salt are not contained in a molecule).

In Formula (I) described above, among the functional groups in $A^1$, the imine residue includes ketimine, aldimine and amidine, and the (thio)carboxylic ester residue includes unsaturated carboxylic ester residues such as acrylate, methacrylate and the like. Metal in the metal salt of the (thio) carboxylic ester residue includes alkali metals, alkali earth metals, Al, Sn, Zn and the like. Thiocarboxylic acid includes both of S-acid and O-acid, and S-acid is preferred.

Among the groups represented by $R^1$, the divalent inactive hydrocarbon group includes preferably an alkylene group having 1 to 20 carbon atoms. This alkylene group may be linear, branched or cyclic, and the linear group is particularly suited. The examples of the above linear alkylene group include methylene, ethylene, trimethylene, tetramethylene, pentamethylene, hexmethylene, octamethylene, decamethylene, dodecamethylene and the like.

$R^2$ and $R^3$ include an alkyl group having 1 to 20 carbon atoms, an alkenyl group having 2 to 20 carbon atoms, an aryl group having 6 to 18 carbon atoms, an aralkyl group having 7 to 18 carbon atoms and the like. In this regard, the alkyl group and the alkenyl group each described above may be linear, branched or cyclic, and the examples thereof include methyl, ethyl, n-propyl, isopropyl, n-butyl, isobutyl, sec-butyl, tert-butyl, pentyl, hexyl, octyl, decyl, dodecyl, cyclopentyl, cyclohexyl, vinyl, propenyl, allyl, hexenyl, octenyl, cyclopentenyl, cyclohexenyl and the like.

The above aryl group may have a substituent such as a lower alkyl group and the like on an aromatic ring, and the examples thereof include phenyl group, tolyl group, xylyl group, naphthyl group and the like.

Further, the above aralkyl group may have a substituent such as a lower alkyl group and the like on an aromatic ring, and the examples thereof include benzyl group, phenethyl group, naphthylmethyl group and the like.

The term n is an integer of 0 to 2 and preferably 0, and it is necessary that an active proton and an onium salt are not contained in the molecule.

The hydrocarbyloxysilane compound represented by Formula (I) includes preferably, for example, (thio)epoxy group-containing hydrocarbyloxysilane compounds such as 2-glycidoxyethyltrimethoxysilane, 2-glycidoxyethyltriethoxysilane, (2-glycidoxyethyl)methyldimethoxysilane, 3-glycidoxypropyltrimethoxysilane, 3-glycidoxypropyltriethoxysilane, (3-glycidoxypropyl)methyldimethoxysilane, 2-(3,4-epoxycyclohexyl)ethyltrimethoxysilane, 2-(3,4-epoxycyclohexyl)ethyltriethoxysilane, 2-(3,4-epoxycyclohexyl)ethyl(methyl)dimethoxysilane and the like and compounds obtained by substituting epoxy groups in the above compounds with thioepoxy groups. Among them, 3-glycidoxypropyltrimethoxysilane and 3-glycidoxypropyltriethoxysilane are particularly suited.

Further, the imine group-containing hydrocarbyloxysilane compound includes preferably N-(1,3-dimethylbutylidene)-3-(triethoxysilyl)-1-propaneamine, N-(1-methylethylidene)-3-(triethoxysilyl)-1-propaneamine, N-ethylidene)-3-(triethoxysilyl)-1-propaneamine, N-(1-methylpropylidene)-3-(triethoxysilyl)-1-propaneamine, N-(4-N,N-dimethylaminobenzylidene)-3-(triethoxysilyl)-1-propaneamine, N-(cyclohexylidene)-3-(triethoxysilyl)-1-propaneamine, and trimethoxysilyl compounds, methyldiethoxysilyl compounds, ethyldiethoxysilyl compounds, methyldimethoxysilyl compounds, ethyldimethoxysilyl compounds and the like corresponding to the above triethoxysilyl compounds. Among them, N-(1-methylpropylidene)-3-(triethoxysilyl)-1-propaneamine and N-(1,3-dimethylbutylidene)-3-(triethoxysilyl)-1-propaneamine are particularly suited. Another examples of the imine residue (amidine group)-containing compound include 1-[3-(triethoxysilyl)propyl]-4,5-dihydroimidazole, 1-[3-(trimethoxysilyl)propyl]-4,5-dihydroimidazole, N-(3-triethoxysilylpropyl)-4,5-dihydroimidazole, N-(3-isopropoxysilylpropyl)-4,5-dihydroimidazole, N-(3-methyldiethoxysilylpropyl)-4,5-dihydroimidazole and the like. Among them, N-(3-triethoxysilylpropyl)-4,5-dihydroimidazole is preferred.

Further, the other hydrocarbyloxysilane compounds include carboxylic ester residue-containing compounds. To be specific, it includes 3-methacryloyloxypropyltriethoxysilane, 3-methacryloyloxypropyltrimethoxysilane, 3-methacryloyloxypropylmethyldiethoxysilane, 3-methacryloyloxypropyltriisopropoxysilane and the like. Among them, 3-methacryloyloxypropyltrimethoxysilane is preferred. The specific examples of the thiocarboxylic ester residue-containing compound include S-3-(triethoxysilyl)propyl octanethioate.

Further, the hydrocarbyloxysilane compound includes isocyanate group-containing compounds. To be specific, it includes 3-isocyanatepropyltrimethoxysilane, 3-isocyanatepropyltriethoxysilane, 3-isocyanatepropylmethyldiethoxysilane, 3-isocyanatepropyltriisopropoxysilane and the like. Among them, 3-isocyanatepropyltriethoxysilane is preferred.

Further, the hydrocarbyloxysilane compound includes carboxylic anhydride residue-containing compounds. To be specific, it includes 3-triethoxysilylpropylsuccinic anhydride, 3-trimethoxysilylpropylsuccinic anhydride, 3-methyldiethoxysilylpropylsuccinic anhydride and the like. Among them, 3-triethoxysilylpropylsuccinic anhydride is preferred.

The above hydrocarbyloxysilane compounds (I) may be used alone or in combination of two or more kinds thereof.

In Formula (II) described above, the non-cyclic tertiary amine residue out of the groups represented by $A^2$ includes N,N-disubstituted aromatic amine residues such as N,N-disubstituted aniline residues, and the cyclic tertiary amine residue can contain a (thio)ether bond as a part of the ring. The divalent inactive hydrocarbon group out of the groups represented by $R^4$ and the groups represented by $R^5$ and $R^6$ each are the same as explained for $R^1$, $R^2$ and $R^3$ in Formula (I) described above. It is necessary that an active proton and an onium salt are not contained in the molecule.

The hydrocarbyloxysilane compound represented by Formula (II) includes, for example, non-cyclic tertiary amine residue-containing hydrocarbyloxysilane compounds such as 3-dimethylaminopropyl(triethoxy)silane, 3-dimethylaminopropyl(trimethoxy)silane, 3-diethylaminopropyl(triethoxy)silane, 3-diethylaminopropyl(trimethoxy)silane, 2-dimethylaminoethyl(triethoxy)silane, 2-dimethylaminoethyl(trimethoxy)silane, 3-dimethylaminopropyl(diethoxy)methylsilane, 3-dibutylaminopropyl(triethoxy)silane and the like. Among them, 3-dimethylaminopropyl(triethoxy)silane and 3-dimethylaminopropyl(trimethoxy)silane are suited.

Further, the cyclic tertiary amine residue-containing hydrocarbyloxysilane compound includes 3-(1-hexamethyleneimino)propyl(triethoxy)silane, 3-(1-hexamethyleneimino)propyl(trimethoxy)silane, (1-hexamethyleneimino)methyl(trimethoxy)silane, (1-hexamethyleneimino)methyl(triethoxy)silane, 2-(1-hexamethyleneimino)ethyl(triethoxy)silane, 2-(1-hexamethyleneimino)ethyl(trimethoxy)silane, 3-(1-pyrrolidinyl)propyl(triethoxy)silane, 3-(1-pyrrolidinyl)propyl(trimethoxy)silane, 3-(1-heptamethyleneimino)propyl(triethoxy)silane, 3-(1-dodecamethyleneimino)propyl(triethoxy)silane, 3-(1-hexamethyleneimino)propyl(diethoxy)methylsilane, 3-(1-hexamethyleneimino)propyl(diethoxy)ethylsilane, 3-[10-(triethoxysilyl)decyl]-4-oxazoline and the like. Among them, 3-(1-hexamethyleneimino)propyl(triethoxy)silane and (1-hexamethyleneimino)methyl(trimethoxy)silane can preferably be given. In particular, 3-(1-hexamethyleneimino)propyl(triethoxy)silane is suited.

Further, the other hydrocarbyloxysilane compounds include 2-(trimethoxysilylethyl)pyridine, 2-(triethoxysilylethyl)pyridine, 2-cyanoethyltriethoxysilane and the like.

The above hydrocarbyloxysilane compounds (II) may be used alone or in combination of two or more kinds thereof.

In Formula (III) described above, the primary amine residue out of the groups represented by $A^3$ includes aromatic amine residues such as an aniline residue, and the non-cyclic secondary amine residue includes N-(monosubstituted) aromatic amine residues such as N-(monosubstituted) aniline residues. Further, the onium salt of the non-cyclic tertiary amine residue includes onium salts of N,N-(disubstituted) aromatic amine residues such as N,N-(disubstituted) aniline residues. In the cases of the cyclic secondary amine residue and the cyclic tertiary amine residue, (thio)ether can be contained as a part of the ring. The divalent inactive hydrocarbon group out of the groups represented by $R^7$ and the groups represented by $R^8$ and $R^9$ each are the same as explained for $R^1$, $R^2$ and $R^3$ in Formula (I) described above.

The hydrocarbyloxysilane compound represented by Formula (III) includes, for example, 3-aminopropyltrimethoxysilane, 3-aminopropyltriethoxysilane, hydroxymethyltrimethoxysilane, hydroxymethyltriethoxysilane, mercaptomethyltrimethoxysilane, mercaptomethyltriethoxysilane, 2-mercaptoethyltrimethoxysilane, 2-mercaptoethyltriethoxysilane, 3-mercaptopropyltrimethoxysilane, 3-mercaptopropyltriethoxysilane, aminophenyltrimethoxysilane, aminophenyltriethoxysilane, 3-(N-methylamino)propyltrimethoxysilane, 3-(N-methylamino)propyltriethoxysilane, octadecyldimethyl(3-trimethylsilylpropyl)ammonium chloride, octadecyldimethyl(3-triethylsilylpropyl)ammonium chloride, cyanomethyltrimethoxysilane, cyanomethyltriethoxysilane, sulfonylmethyltrimethoxysilane, sulfonylmethyltriethoxysilane sulfinylmethyltrimethoxysilane, sulfinylmethyltriethoxysilane and the like.

Among them, particularly preferred are mercaptomethyltrimethoxysilane, mercaptomethyltriethoxysilane, 2-mercaptoethyltrimethoxysilane, 2-mercaptoethyltriethoxysilane, 3-mercaptopropyltrimethoxysilane and 3-mercaptopropyltriethoxysilane.

The above hydrocarbyloxysilane compounds (III) may be used alone or in combination of two or more kinds thereof.

The hydrocarbyloxysilane compound represented by Formula (IV) described above and/or the partially condensed products thereof can be used for the hydrocarbyloxysilane compounds of (4) described above. In this case, the partially condensed products are the same as described in Formula (I).

The hydrocarbyloxysilane compound represented by Formula (IV) includes suitably bis(3-triethoxysilylpropyl)tetrasulfide, bis(2-triethoxysilylethyl)tetrasulfide, bis(3-trimethoxypropyl)tetrasulfide, bis(2-trimethoxysilylethyl)tetrasulfide, bis(3-triethoxysilylpropyl)trisulfide, bis(2-triethoxysilylethyl)trisulfide, bis(3-trimethoxypropyl)trisulfide, bis(2-trimethoxysilylethyl)trisulfide, bis(3-triethoxysilylpropyl)disulfide, bis(2-triethoxysilylethyl)disulfide, bis(3-trimethoxypropyl)disulfide, bis(2-trimethoxysilylethyl)disulfide and mixtures containing at least one of the above compounds. Among the compounds described above, the commercially available compound includes trade name Si69 (manufactured by Degussa AG.) comprising bis(3-triethoxysilylpropyl)tetrasulfide (hereinafter referred to as TESPT) as a principal component.

Further, the hydrocarbyloxysilane compound represented by Formula (V) described above and/or the partially condensed products thereof can be used for the hydrocarbyloxysilane compounds of (5) described above. In this case, the partially condensed products are the same as described in Formula (I). In Formula (V) described above, $R^{12}$ and $R^{13}$ are the same as explained for $R^2$ and $R^3$ in Formula (I) described above.

The hydrocarbyloxysilane compound represented by Formula (V) includes, for example, tetramethoxysilane, tetraethoxysilane, tetra-n-propoxysilane, tetraisopropoxysilane, tetra-n-butoxysilane, tetraisobutoxysilane, tetra-sec-butoxysilane, tetra-tert-butoxysilane, methyltrimethoxysilane, methyltriethoxysilane, methyltripropoxysilane, methyltriisopropoxysilane, ethyltrimethoxysilane, ethyltriethoxysilane, propyltriethoxysilane, butyltrimethoxysilane, n-octyltriethoxysilane, phenyltrimethoxysilane, phenyltriethoxysilane, dimethyldimethoxysilane, methylphenyldimethoxysilane, vinyltrimethoxysilane, vinyltriethoxysilane, divinyldimethoxysilane, divinyldiethoxysilane and the like.

The above hydrocarbyloxysilane compounds (V) may be used alone or in combination of two or more kinds thereof.

Further, the hydrocarbyloxysilane compounds represented by Formulas (I) to (V) described above may be used in combination of two or more kinds thereof.

Next, the organic metal compound used for producing the activated silane compound of the present invention shall be explained. This organic metal compound is at least one compound selected from the group consisting of (6) to (9) shown below, and the organic metal compound may be used alone or in combination of two or more kinds thereof.

(6) Carboxylate of Tin Having an Oxidation Number of 2 Represented by Formula (VI)

$$Sn(OCOR^{14})_2 \quad (VI)$$

(wherein $R^{14}$ is a hydrocarbon group having 2 to 19, and two $OCOR^{14}$ may be the same or different).

(7) Compound of Tin Having an Oxidation Number of 4 Represented by Formula (VII)

$$R^{15}{}_rSnA^4{}_tB^1{}_{(4-t-r)} \quad (VII)$$

(wherein r is an integer of 1 to 3; t is an integer of 1 or 2; t+r is an integer of 3 or 4; $R^{15}$ represents an aliphatic hydrocarbon group having 1 to 30 carbon atoms, and when $R^{15}$ is present in a plural number, they may be the same or different; $B^1$ is a hydroxyl group or halogen; $A^4$ is a group selected from (a) a carboxyl group having 2 to 30 carbon atoms, (b) a 1,3-dicarbonyl-containing group having 5 to 30 carbon atoms, (c) a hydrocarbyloxy group having 3 to 30 carbon atoms and (d) a siloxy group trisubstituted (may be the same or different) in total with a hydrocarbon group having 1 to 20 carbon atoms and/or a hydrocarbyloxy group having 1 to 20 carbon atoms, and when plural $A^4$ are present, they may be the same or different).

(8) Titanium Compound Having an Oxidation Number of 4 Represented by Formula (VIII)

$$A^5{}_xTiB^2{}_{(4-x)} \quad (VIII)$$

(wherein x is an integer of 2 or 4; $A^5$ is (a) a hydrocarbyloxy group having 2 to 30 carbon atoms or (b) a siloxy group trisubstituted in total with an alkyl group having 1 to 30 carbon atoms and/or a hydrocarbyloxy group having 1 to 20 carbon atoms, and when plural $A^5$ is present in a plural number, they may be the same or different; $B^2$ is a 1,3-dicarbonyl-containing group having 5 to 30 carbon atoms, and when $B^2$ is present in a plural number, they may be the same or different).

(9) Aluminum Compound Having an Oxidation Number of 3 Represented by Formula (IX)

$$Al(OR^{16})_3 \quad (IX)$$

(wherein $R^{16}$ is a hydrocarbon group having 1 to 30 carbon atoms).

The carboxylate of tin having an oxidation number of 2 represented by Formula (VI) in (6) described above is preferably at least one organic metal compound selected from tin bis(2-ethylhexanoate), tin dioleate and tin dilaurate.

Among the compounds of tin having an oxidation number of 4 represented by Formula (VII) in (7) described above, (a) the carboxylate of tin includes suitably dicarboxylate of tetravalent dihydrocarbyltin (including bis(hydrocarbyldicarboxylic acid) salts) and monocarboxylate hydroxide; (b) the compound having a 1,3-dicarbonyl-containing group having 5 to 30 carbon atoms includes suitably bis(1,3-diketonate); (c) the compound having a hydrocarbyloxy group having 2 to 30 carbon atoms includes suitably alkoxy halides; and (d) the compound having a siloxy group trisubstituted (may be the same or different) in total with a hydrocarbon group having 1 to 20 carbon atoms and/or a hydrocarbyloxy group having 1 to 20 carbon atoms includes suitably alkoxy(trihydrocarbyl oxide), alkoxy(dihydrocarbylalkoxy siloxide), bis(trihydrocarbyl siloxide), bis(dihydrocarbylalkoxy siloxide) and the like. The hydrocarbon group bonded to tin is preferably a group having 4 or more carbon atoms, more preferably 4 to 8 carbon atoms. The dicarboxylate of tetravalent dihydrocarbyltin is particularly preferably dibutyltin dilaurate and dioctyltin dilaurate.

The titanium compound having an oxidation number of 4 represented by Formula (VIII) in (8) described above includes tetraalkoxide or tetrakis(trihydrocarbylalkoxy siloxide) of titanium having an oxidation number of 4 or a titanium chelate compound represented by Formula (X) shown below:

$$(R^{17}O)_2Ti[CH_3-(C=O)-CH-(C=O)-CH_3]_2 \quad (X)$$

(wherein $R^{17}O$ is a hydrocarbyloxy group having 2 to 30 carbon atoms and may be the same or different).

Among them, titanium (IV) 2-ethyl-1,3-hexanedioleate or diisopropoxybis(acetylacetonate)titanium which is one example of the titanium chelate compound represented by Formula (X) is particularly suitably used.

Further, the aluminum compound having an oxidation number of 3 represented by Formula (IX) in (9) described above includes tri-tert-butoxyaluminum, tri-sec-butoxyaluminum and the like. Among them, tri-tert-butoxyaluminum and tri-sec-butoxyaluminum are particularly preferred.

The organic solvent used in producing the activated silane compound of the present invention may be any ones as long as they dissolve the hydrocarbyloxysilane compounds and the organic metal compounds, and they include hydrocarbon solvents such as cyclohexane and the like, alcohols such as ethanol, butanol, pentanol and the like and cyclic or linear ethers such as tetrahydrofuran, methyl ethyl ketone and the like.

The above solvents may be used alone or, if necessary, in combination of two or more kinds thereof. A required amount of water may be used according to the kinds of the hydrocarbyloxysilane compound and the organic metal compound. Water is suitably used alone or in the forms of a solution of alcohol and the like and a micelle dispersed in a hydrocarbon solvent, and in addition thereto, water which is potentially contained in a compound capable of releasing water in a reaction system, such as water adsorbed on a surface of a solid matter, hydrated water of hydrates and the like can effectively be used as well if necessary. Accordingly, combined use of the metal compounds described above with compounds such as solid mattress having adsorbed water, hydrates and the like which can readily release water is included in the preferred embodiment.

The hydrocarbyloxysilane compound and the organic metal compound each described above may be added separately to the reaction system or in the form of a mixture prepared by mixing them immediately before used, but storage of the mixture over a long period of time brings about decomposition of the metal compound and therefore is not preferred.

The use amounts of the above organic metal compound and water used if necessary are selected preferably so that a mole ratio thereof based on the combined amount of the metal in the organic metal compound and the hydrocarbyloxysilane compound present in the system is 0.1 or more for both of them.

The reaction of the hydrocarbyloxysilane compound with the organic metal compound is carried out preferably at a temperature of 20° C. or higher under the atmosphere of inert gas such as nitrogen and the like, and it is carried out usually at room temperature. However, it may be carried out, if necessary, under heating at a temperature falling in a range of 30 to 120° C. The reaction is carried out preferably at a reaction time of 30 to 300 minutes.

The activated silane compound of the present invention produced in the manner described above contains preferably 10 to 180 parts by mass of silica per 100 parts by mass of the rubber component. Further, in this rubber composition, the activated silane compound is blended in an amount of 1 to 20 mass %, preferably 1 to 15 mass %, more preferably 1 to 15 mass %, further preferably 3 to 15 mass % and particularly preferably 5 to 15 mass % based on the silica.

The silica used for the rubber composition of the present invention shall not specifically be restricted, and products optionally selected from those which have so far been conventionally used as a reinforcing filler can be used.

The above silica includes, for example, wet silica (hydrous silica), dry silica (silicic anhydride) and the like, and among them, wet silica which exerts most notably an effect of improving a fracture characteristic, an abrasion resistance and a low heating property is preferred. A nitrogen adsorbing specific surface area ($N_2SA$, according to a BET method) of silica is preferably 100 to 500 m$^2$/g. Suited wet silica includes AQ, VN3, LP, NA and the like each manufactured by Tosoh Silica Corporation and Ultrasil VN3 ($N_2SA$: 210 m$^2$/g) manufactured by Degussa AG.

The silica described above is blended preferably in an amount of 10 to 180 parts by mass per 100 parts by mass of the rubber component from the viewpoints of a physical property-improving effect and a kneading workability.

In the present invention, carbon black and/or an inorganic filler represented by the following Formula (XI) in addition to the silica described above may be further blended, if necessary, in an amount of 5 to 100 parts by mass for the purpose of improving the physical properties and the like:

(wherein $M^1$ is metal selected from the group consisting of aluminum, magnesium, titanium, calcium and zirconium or at least one selected from oxides or hydroxides of the above metals, hydrates thereof and carbonates of the above metals; m, x, y and z each are an integer of 1 to 5, an integer of 0 to 10, an integer of 2 to 5 and an integer of 0 to 10; when both of x and z are 0 in the formula described above, the above inorganic compound is at least one metal selected from aluminum, magnesium, titanium, calcium and zirconium, metal oxide or metal hydroxide).

The carbon black described above includes, for example, FEF, GPF, SRF, HAF, N339, IISAF, ISAF, SAF and the like. A nitrogen adsorption specific surface area ($N_2SA$, according to JIS K 6217-2: 2001) of carbon black is preferably 20 to 160 m$^2$/g, more preferably 70 to 160 m$^2$/g. Further, it is preferably carbon black having a dibutyl phthalate absorption (DBP, according to JIS K 6217-4: 2001) of 80 to 170 cm$^3$/100 g. An effect of improving the various physical properties, particularly the rupture characteristic grows large by using the above carbon blacks. Preferred carbon black is HAF, N339, IISAF, ISAF and SAF.

Capable of being used as the inorganic filler represented by Formula (XI) are alumina ($Al_2O_3$) such as γ-alumina, α-alumina and the like, alumina monohydrate ($Al_2O_3.H_2O$) such as boehmite, diaspore and the like, aluminum hydroxide (Al(OH)$_3$) such as gibbsite, bayerite and the like, aluminum carbonate ($Al_2(CO_3)_2$), magnesium hydroxide (Mg(OH)$_2$), magnesium oxide (MgO), magnesium carbonate (MgCO$_3$), talc (3MgO.4SiO$_2$.H$_2$O), attapulgite (5MgO.8SiO$_2$.9H$_2$O), titan white (TiO$_2$), titan black (TiO$_{2n-1}$), calcium oxide (CaO), calcium hydroxide (Ca(OH)$_2$), magnesium aluminum oxide (MgO.Al$_2$O$_3$), clay (Al$_2$O$_3$.2SiO$_2$), kaolin (Al$_2$O$_3$.2SiO$_2$.2H$_2$O) pyrophyllite (Al$_2$O$_3$.4SiO$_2$.H$_2$O), bentonite (Al$_2$O$_3$.4SiO$_2$.2H$_2$O), aluminum silicate (Al$_2$SiO$_5$, Al$_4$.3SiO$_4$.5H$_2$O and the like), magnesium silicate (Mg$_2$SiO$_4$, MgSiO$_3$ and the like), calcium silicate (Ca$_2$.SiO$_4$ and the like), calcium aluminum silicate (Al$_2$O$_3$.CaO.2SiO$_2$ and the like), calcium magnesium silicate (CaMgSiO$_4$), calcium carbonate (CaCO$_3$), zirconium oxide (ZrO$_2$), zirconium hydroxide (ZrO(OH)$_2$.nH$_2$O), zirconium carbonate (Zr(CO$_3$)$_2$) and crystalline aluminosilicate containing hydrogen, alkali metal or alkali earth metal which corrects a charge, such as various zeolites. Among them, the inorganic fillers in which $M^1$ in Formula (XI) described above is selected from aluminum metal, oxide or hydroxide of aluminum, hydrate thereof and carbonate of aluminum are preferred, and aluminum hydroxide is particularly preferred.

Optional rubbers which have so far been blended usually for various rubber compositions, for example, natural rubber (NR), polyisoprene rubber (IR), various styrene-butadiene copolymer rubbers (SBR), various polybutadiene rubbers (BR), acrylonitrile-butadiene copolymer rubbers (NBR), diene base rubbers such as butyl rubber, ethylene-propylene copolymer rubbers (EPR, EPDM) and the like can be used as the rubber used for the rubber component of the rubber composition of the present invention in the form of a single component or an optional blend.

Various chemicals which have so far been used usually in the rubber industry, for example, vulcanizing agents, vulcanization accelerating agents, process oils, antioxidants, scorch preventives, zinc oxide, stearic acid and the like can be added to the rubber composition of the present invention as long as the object of the present invention is not damaged.

The vulcanizing agent described above includes sulfur and the like, and a use amount thereof is preferably 0.1 to 10.0 parts by mass, more preferably 0.5 to 5.0 parts by mass in terms of a sulfur content based on 100 parts by mass of the rubber component.

The vulcanization accelerating agent which can be used in the present invention shall not specifically be restricted and includes, for example, thiazole base vulcanization accelerating agents such as M (2-mercaptobenzothiazole), DM (benzothiazyl disulfide), CZ (N-cyclohexyl-2-benzothiazylsulfenamide) and the like and guanidine base vulcanization accelerating agents such as DPG (diphenylguanidine) and the like. A use amount thereof is preferably 0.1 to 5.0 parts by mass, more preferably 0.2 to 3.0 parts by mass per 100 parts by mass of the rubber component.

Further, the process oil which can be used for the rubber composition of the present invention includes, for example, a paraffin base, a naphthene base, an aromatic base and the like. A use amount thereof is preferably 0 to 100 parts by mass per 100 parts by mass of the rubber component. If it is 100 parts by mass or less, the vulcanized rubber is improved in a tensile strength and a low heating property.

The rubber composition of the present invention is obtained by kneading with a kneading machine such as a Banbury mixer, a roll, an internal mixer and the like, and it is vulcanized after molding processing and used for members such as, for example, tire tread, undertread, sidewalls, carcass coating rubber, belt coating rubber, bead fillers, chafer, bead coating rubber and the like in tire use.

The pneumatic tire of the present invention is produced by a conventional process using the rubber composition of the present invention described above. That is, the rubber composition of the present invention blended with various chemicals as described above is processed, if necessary, into respective members in a stage in which it is not yet vulcanized, and the respective members are stuck and molded in a tire building machine to form an uncured tire. This uncured tire is heated and pressurized in a vulcanizing machine to obtain a tire.

The pneumatic tire of the present invention thus obtained is excellent in a durability and a low heating property.

EXAMPLES

Next, the present invention shall be explained in further details with reference to examples, but the present invention shall by no means be restricted by these examples.

A Mooney viscosity of unvulcanized rubbers of rubber compositions obtained in the respective examples and the physical properties of the vulcanized rubbers were measured according to following methods.
(1) Mooney Viscosity:
  $ML_{1+4}$ was measured at 130° C. according to JIS K 6300: 2001.
(2) Rupture Characteristics:
  A dumbbell-like No. 3 type test piece was used to carry out a tensile test according to JIS K 6251: 2004 to measure a tensile stress at break (TSb, unit: MPa) and an elongation at break (Eb, unit: %). The larger the measured value is, the better the rupture characteristics are.
(3) Abrasion Resistance:
  I (abrasion resistance index (%)) was measured according to JIS K 6264-2: 2005 improved Lambourn abrasion test, and this numerical value was shown by an index, wherein a data obtained in Comparative Example 1 was set to 100. The larger the numerical value is, the better the abrasion resistance is.
(4) Low Heating Property:
  A spectrometer (dynamic viscoelasticity measuring test machine) manufactured by Ueshima Seisakusho Co., Ltd. was used to measure tan δ at a frequency of 52 Hz, an initial strain of 10%, a measuring temperature of 60° C. and a dynamic strain of 1%. The smaller the measured value is, the better the low heating property is.

Production Example 1

Preparation of Reaction Product of TESPT and Tin Dioleate (Oxidation Number: 2)

A reaction product of TESPT (trade name Si69 manufactured by Degussa AG. was used) and tin dioleate (oxidation number: 2) was prepared in the following manner.

A flask of 300 ml was charged with 100 ml of deoxidized cyclohexane under nitrogen atmosphere and further charged with 0.05 mole of Si69, and the mixture was stirred well. A cyclohexane 50 ml solution of 0.05 mole of tin dioleate (oxidation number: 2) which was substituted with nitrogen was dropwise added slowly to the above solution at room temperature, and then the solution was stirred for 15 minutes. A hot bath of 50° C. was used to remove the solvent from the above solution in 30 minutes under a reduced pressure of 26.7 hPa by means of an evaporator. Further, the solution was then maintained at 1.33 hPa or lower, whereby the solvent component was completely removed to obtain an activated silane compound.

Production Example 2

Preparation of Reaction Product of TESPT and Tin Dibutyldioleate (Oxidation Number: 4)

Preparation was carried out by the same method as in Production Example 1, except that tin dibutyldioleate was used in place of tin dioleate.

Production Example 3

Preparation of Reaction Product of TESPT and Titanium (IV) 2-Ethyl-1,3-Hexanedioleate (Oxidation Number: 4, Manufactured by Sigma-Aldrich Co., Ltd.)

Preparation was carried out by the same method as in Production Example 1, except that titanium (IV) 2-ethyl-1,3-hexanedioleate (manufactured by Sigma-Aldrich Co., Ltd.) was used in place of tin dioleate.

Production Example 4

Preparation of Reaction Product of 3-Mercaptopropyltriethoxysilane, n-Octyltriethoxysilane and Tin Dibutyloleate (Oxidation Number: 4)

Preparation was carried out by the same method as in Production Example 1, except that 0.01 mole of 3-mercaptopropyltriethoxysilane (manufactured by Gelest Inc.) and 0.04 mole of n-octyltriethoxysilane (manufactured by Tokyo Kasei Kogyo Co., Ltd.) were used in place of TESPT and that tin dibutyldioleate was used in place of tin dioleate.

Production Example 5

Preparation of reaction product of S-3-(triethoxysilyl)propyl octanethioate and tin dioleate Preparation was carried out by the same method as in Production Example 1, except that S-3-(triethoxysilyl)propyl octanethioate (trade name: NXT Silane, manufactured by General Electric Company) was used in place of TESPT.

Examples 1 to 8 and Comparative Examples 1 to 6

Rubber compositions were prepared in Examples 1 to 8 and Comparative Examples 1 to 6 according to blend formulations shown in Table 2 based on blend formulations shown in Table 1. Then, the Mooney viscosity, the tensile stress at break, the elongation at break, the abrasion resistance and the low heating property were tested by the test methods described above. The results thereof are shown in Table 2.

TABLE 1

| Blend formulation | Mass part |
| --- | --- |
| SBR *1 | 100 |
| Silica *2 | 50 |
| Activated silane compound *3 | Refer to Table 2 |
| Silica dispersant *4 | Refer to Table 2 |
| Aroma oil | 20 |
| Stearic acid | 2 |
| Zinc oxide | 3 |
| Antioxidant 6C *5 | 1 |
| Vulcanization accelerating agent D *6 | 0.4 |
| Vulcanization accelerating agent NS *7 | 1 |
| Sulfur | 1.75 |

Remarks:
*1: SBR 1500, styrene content = 23.5 mass %, vinyl bonding amount = 18 %, manufactured by JSR Corporation
*2: Wet silica, trade name: Nipsil AQ, manufactured by Tosoh Silica Corporation
*3: Activated silane compounds described in Production Examples 1 to 5, silane coupling agents 1 to 3 and a tin catalyst (tin bis(2-ethylhexanoate) (oxidation number: 2))
*4: n-Octyltriethoxysilane
*5: N-1,3-dimethylbutyl)-N'-phenyl-p-phenylenediamine, trade name: Nocrac 6C, manufactured by Ouchi Shinko Chemical Industrial Co., Ltd.
*6: 1,3-diphenylguanidine, trade name: Nocceler D, manufactured by Ouchi Shinko Chemical Industrial Co., Ltd.
*7: N-t-butyl-2-benzothiazolylsulfenamide, trade name: Nocceler NS, manufactured by Ouchi Shinko Chemical Industrial Co., Ltd.

TABLE 2

| Blend formulation (mass part) | Example | | | | | | | | Comparative Example | | | | | |
| --- | --- | --- | --- | --- | --- | --- | --- | --- | --- | --- | --- | --- | --- | --- |
| | 1 | 2 | 3 | 4 | 5 | 6 | 7 | 8 | 1 | 2 | 3 | 4 | 5 | 6 |
| Silane coupling agent 1 *A | — | — | — | — | — | — | — | — | — | 5 | — | — | — | — |
| Silane coupling agent 2 *B | — | — | — | — | — | — | — | — | — | — | 5 | — | — | — |
| Silane coupling agent 3 *C | — | — | — | — | — | — | — | — | — | — | — | 7 | — | — |
| Activated silane compound described in Production Example 1 | 5 | 2.5 | 1.5 | 0.5 | — | — | — | — | — | — | — | — | — | — |
| Activated silane compound described in Production Example 2 | — | — | — | — | 5 | — | — | — | — | — | — | — | — | — |
| Activated silane compound described in Production Example 3 | — | — | — | — | — | 5 | — | — | — | — | — | — | — | — |
| Activated silane compound described in Production Example 4 | — | — | — | — | — | — | 5 | — | — | — | — | — | — | — |
| Activated silane compound described in Production Example 5 | — | — | — | — | — | 5 | — | 7 | — | — | — | — | — | — |
| Tin bis(2-ethylhexanoate (oxidation number: 2) | — | — | — | — | — | — | — | — | — | — | — | — | 5 | — |
| Silica dispersant (refer to Table 1) | — | — | — | — | — | — | — | — | — | — | — | — | — | 5 |
| Evaluation results | | | | | | | | | | | | | | |
| Mooney viscosity (ML1 + 4: 130° C.) | 60 | 63 | 80 | 100 | 64 | 64 | 64 | 46 | 110 | 65 | 68 | 52 | 105 | 62 |
| tensile stress at break [TSb (MPa)] | 23.5 | 22.7 | 22 | 20.5 | 23 | 23.6 | 29.7 | 25.7 | 19.5 | 22.5 | 23 | 25.2 | 20.5 | 20 |

TABLE 2-continued

| Blend formulation | Example | | | | | | | | Comparative Example | | | | | |
|---|---|---|---|---|---|---|---|---|---|---|---|---|---|---|
| (mass part) | 1 | 2 | 3 | 4 | 5 | 6 | 7 | 8 | 1 | 2 | 3 | 4 | 5 | 6 |
| Elongation at break [Eb (%)] | 515 | 490 | 480 | 460 | 551 | 551 | 508 | 508 | 435 | 475 | 489 | 513 | 440 | 515 |
| Abrasion resistance (index) | 130 | 125 | 118 | 115 | 126 | 126 | 124 | 126 | 100 | 125 | 120 | 123 | 102 | 105 |
| Low heating property (tan δ) | 0.10 | 0.11 | 0.12 | 0.13 | 0.11 | 0.10 | 0.10 | 0.11 | 0.16 | 0.13 | 0.12 | 0.12 | 0.15 | 0.15 |

Remarks:
*A: TESPT (trade name Si69, manufactured by Degussa AG.)
*B: S-3-triethoxysilylpropyl octanethioate (trade name: NXT Silane, manufactured by General Electric Company)
*C: mixture of 3-mercaptopropyltriethoxysilane (manufactured by Gelest Inc.)/n-octyltriethoxysilane (manufactured by Tokyo Kasei Kogyo Co., Ltd.) = 20/80 (mole ratio)

As can be seen from the results shown in Table 2, the rubber compositions of the present invention (Examples 1 to 8) were improved in a fracture characteristic, an abrasion resistance and a low heating property as compared with the rubber composition prepared in Comparative Example 1. Further, they had a low Mooney viscosity and showed a good workability.

Further, as apparent from comparison of the results obtained in Examples 1 to 8 with those obtained in Comparative Examples 1 to 6, the activated silane compounds of the present invention could be reduced in a blending amount as compared with conventional activated silane compounds.

Examples 9 to 16 and Comparative Examples 7 to 12

The rubber compositions prepared in Examples 1 to 8 and Comparative Examples 1 to 6 each were provided on a tread of a radial tire for passenger cars having a size of 185/60R14 to produce fourteen kinds of tires for trial use in Examples 9 to 16 and Comparative Examples 7 to 12, and the abrasion resistance and the low heating property were evaluated. The tires produced in Examples 9 and 13 to 16 were excellent in both of an abrasion resistance and a low heating property as compared with the tires produced in Comparative Examples 8 to 12.

Further, the tires produced in Examples 9 to 16 were excellent in both of an abrasion resistance and a low heating property as compared with the tire produced in Comparative Examples 7.

According to the present invention, enhancing interaction of silica with carbon black and improving the fracture characteristic, the abrasion resistance and the low heating property make it possible to provide an activated silane compound which can be reduced in a blending amount, a rubber composition prepared by blending it as a silane coupling agent and a pneumatic tire prepared by using the above rubber composition, which is excellent in a durability, a low heating property and the like.

INDUSTRIAL APPLICABILITY

The activated silane compound of the present invention enhances interaction of silica with carbon black and improves the fracture characteristic, the abrasion resistance and the low heating property, and therefore it is suitably blended into various rubber compositions, particularly silica-blended rubber compositions. The above rubber compositions are suitably used for treads, sidewalls, various case members and the like in radial tires for passenger cars, radial tires for light cars, radial tires for light trucks, radial tires for trucks and buses, radial tires for construction vehicles and the like. Further, they are suitably used as well for various industrial rubber products, for example, belt conveyors, hoses, rubber lashers, quake-absorbing rubbers and the like.

What is claimed is:

1. A rubber composition comprising 10 to 180 parts by mass of silica per 100 parts by mass of a rubber component and 3 to 15 mass % of an activated silane compound based on silica,
   wherein the activated silane compound is obtained by reacting a hydrocarbyloxysilane compound with an organic metal compound in an organic solvent, and
   wherein the hydrocarbyloxysilane compound is at least one compound selected from the group consisting of bis(2-trimethoxysilylethyl) trisulfide, bis(3-triethoxysilylpropyl) disulfide, bis(2-triethoxysilylethyl) disulfide, bis(3-trimethoxypropyl) disulfide, bis(2-trimethoxysilylethyl) disulfide, bis(2-triethoxysilylethyl) trisulfide, and bis(3-trimethoxypropyl)trisulfide.

2. The rubber composition according to claim 1, wherein the organic metal compound is at least one compound selected from the group consisting of (6) to (9) shown below:
   (6) carboxylate of tin having an oxidation number of 2 represented by Formula (VI)

$$Sn(OCOR^{14})_2 \qquad (VI)$$

(wherein $R^{14}$ is a hydrocarbon group having 2 to 19, and two $OCOR^{14}$ may be the same or different);
   (7) a compound of tin having an oxidation number of 4 represented by Formula (VII)

$$R^{15}_r SnA^4_t B^1_{(4-t-r)} \qquad (VII)$$

(wherein r is an integer of 1 to 3; t is an integer of 1 or 2; t+r is an integer of 3 or 4; $R^{15}$ represents an aliphatic hydrocarbon group having 1 to 30 carbon atoms, and when $R^{15}$ is present in a plural number, they may be the same or different; $B^1$ is a hydroxyl group or halogen; $A^4$ is a group selected from (a) a carboxyl group having 2 to 30 carbon atoms, (b) a 1,3-dicarbonyl-containing group having 5 to 30 carbon atoms, (c) a hydrocarbyloxy group having 3 to 30 carbon atoms and (d) a siloxy group trisubstituted (may be the same or different) in total with a hydrocarbon group having 1 to 20 carbon atoms and/or a hydrocarbyloxy group having 1 to 20 carbon atoms, and when $A^4$ is present in a plural number, they may be the same or different);

(8) titanium compound having an oxidation number of 4 represented by Formula (VIII)

$$A^5{}_x TiB^2{}_{(4-x)} \tag{VIII}$$

(wherein x is an integer of 2 or 4; $A^5$ is (a) a hydrocarbyloxy group having 2 to 30 carbon atoms or (b) a siloxy group trisubstituted in total with an alkyl group having 1 to 30 carbon atoms and/or a hydrocarbyloxy group having 1 to 20 carbon atoms, and when $A^5$ is present in a plural number, they may be the same or different; $B^2$ is a 1,3-dicarbonyl-containing group having 5 to 30 carbon atoms, and when $B^2$ is present in a plural number, they may be the same or different);

(9) aluminum compound having an oxidation number of 3 represented by Formula (IX)

$$Al(OR^{16})_3 \tag{IX}$$

(wherein $R^{16}$ is a hydrocarbon group having 1 to 30 carbon atoms).

3. The rubber composition according to claim 2, wherein the carboxylate of tin having an oxidation number of 2 represented by Formula (VI) is at least one organic metal compound selected from tin bis(2-ethylhexanoate), tin dioleate and tin dilaurate.

4. A rubber composition comprising 10 to 180 parts by mass of silica per 100 parts by mass of a rubber component and 1 to 20 mass % of an activated silane compound based on silica,
wherein the activated silane compound is obtained by reacting a hydrocarbyloxysilane compound with an organic metal compound in an organic solvent, and wherein the hydrocarbyloxysilane compound is at least one compound selected from the group consisting of bis(2-trimethoxysilylethyl) trisulfide, bis(3-triethoxysilylpropyl) disulfide, bis(2-triethoxysilylethyl) disulfide, bis(3-trimethoxypropyl) disulfide, bis(2-trimethoxysilylethyl) disulfide, bis(2-triethoxysilylethyl) trisulfide, and bis(3-trimethoxypropyl)trisulfide.

5. The rubber composition according to claim 4, further comprising carbon black and/or an inorganic filler represented by the following Formula (XI) in an amount of 5 to 100 parts by mass per 100 parts by mass of the rubber component:

$$mM^1 \cdot xSiO_y \cdot zH_2O \tag{XI}$$

(wherein $M^1$ is a metal selected from the group consisting of aluminum, magnesium, titanium, calcium and zirconium or at least one selected from oxides or hydroxides of the above metals, hydrates thereof and carbonates of the above metals; m, x, y and z each are an integer of 1 to 5, an integer of 0 to 10, an integer of 2 to 5 and an integer of 0 to 10; when both of x and z are 0 in the formula described above, the above inorganic compound is at least one metal selected from aluminum, magnesium, titanium, calcium and zirconium, metal oxide or metal hydroxide).

6. A tire prepared by using the rubber composition according to claim 1 for a part of members thereof.

7. A tire prepared by using the rubber composition according to claim 4 for a part of members thereof.

* * * * *